(12) United States Patent
Haras et al.

(10) Patent No.: US 7,672,711 B2
(45) Date of Patent: Mar. 2, 2010

(54) METHOD AND SYSTEM FOR PROVIDING TOMOGRAPHIC PICTURES OF A PATIENT BY USING CONTRAST MEDIUM INJECTIONS

(75) Inventors: Gabriel Haras, Mücke (DE); Andreas Mahnken, Aachen (DE); Annabella Rauscher-Scheibe, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 221 days.

(21) Appl. No.: 11/513,182

(22) Filed: Aug. 31, 2006

(65) Prior Publication Data

US 2007/0066892 A1 Mar. 22, 2007

(30) Foreign Application Priority Data

Sep. 1, 2005 (DE) ........................ 10 2005 041 626

(51) Int. Cl.
*A61B 6/00* (2006.01)
(52) U.S. Cl. ........................ 600/431; 600/425; 600/428; 600/407; 378/8
(58) Field of Classification Search ................. 600/431, 600/420; 378/8
See application file for complete search history.

(56) References Cited

U.S. PATENT DOCUMENTS

| 6,231,834 B1 * | 5/2001 | Unger et al. ................ 424/9.51 |
| 6,236,706 B1 * | 5/2001 | Hsieh ............................. 378/8 |
| 6,385,483 B1 * | 5/2002 | Uber et al. ................... 600/431 |
| 6,535,821 B2 * | 3/2003 | Wang et al. .................... 702/19 |
| 2002/0010551 A1 | 1/2002 | Wang et al. |
| 2006/0239918 A1 * | 10/2006 | Klotz et al. ................... 424/9.3 |
| 2006/0264898 A1 * | 11/2006 | Beasley et al. .............. 604/506 |
| 2007/0255135 A1 * | 11/2007 | Kalafut et al. .............. 600/431 |
| 2008/0253634 A1 * | 10/2008 | Hay et al. .................... 382/130 |

FOREIGN PATENT DOCUMENTS

| DE | 10 2005 006 657.7 | 2/2005 |
| DE | 10 2005 006 659.3 | 2/2005 |

* cited by examiner

*Primary Examiner*—Long Ve Le
*Assistant Examiner*—Nigel Fontenot
(74) *Attorney, Agent, or Firm*—Harness, Dickey & Pierce, P.L.C.

(57) ABSTRACT

A method is disclosed for providing tomographic pictures of a patient with the aid of a tomographic system by using contrast medium injections. The patient is firstly injected with a defined test bolus, while the temporal concentration profile of the contrast medium in at least one body region is determined in at least one scanning plane. The functional parameters of a prediction model that maps or at least approximates the relationship between the profile of a contrast medium injection and the temporal profile of the contrast medium concentration in the body region are determined from the measured profile of the contrast medium concentration in relation to the profile of the test bolus injection. After the specification of a desired contrast in the body region, the profile of a contrast medium injection that is required therefore is automatically calculated in temporal relationship with the scan, and the start of the tomographic scan and the start of the contrast medium injection and the profile thereof are started automatically in a fashion temporally tuned to one another.

26 Claims, 4 Drawing Sheets

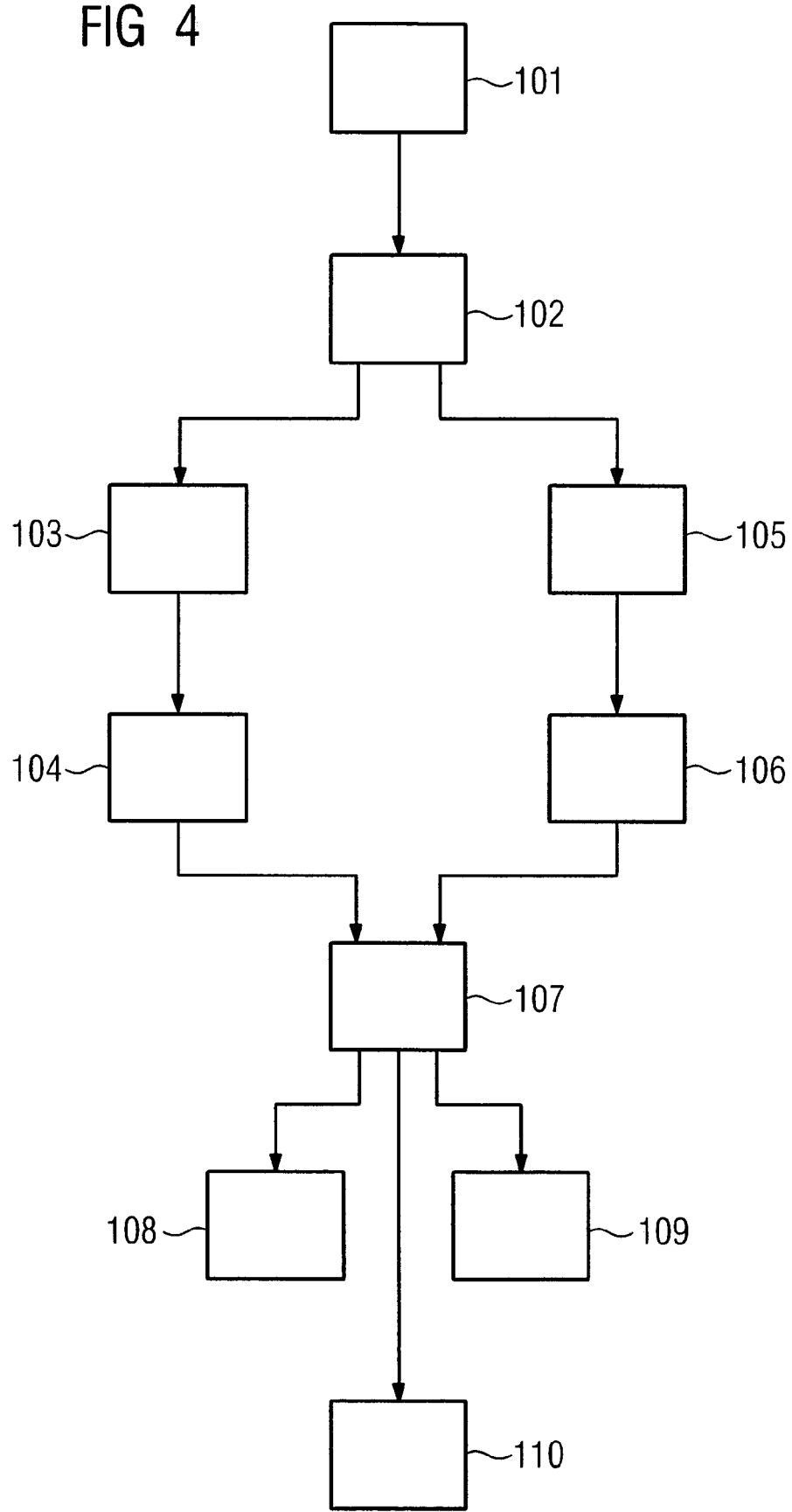

US 7,672,711 B2

METHOD AND SYSTEM FOR PROVIDING TOMOGRAPHIC PICTURES OF A PATIENT BY USING CONTRAST MEDIUM INJECTIONS

PRIORITY STATEMENT

The present application hereby claims priority under 35 U.S.C. §119 on German patent application number DE 10 2005 041 626.8 filed Sep. 1, 2005, the entire contents of which is hereby incorporated herein by reference.

FIELD

The invention generally relates to a method for providing tomographic pictures of a patient with the aid of a tomographic system. For example, it may relate to a method using contrast medium injections, wherein the patient is firstly injected with a defined test bolus, while the temporal concentration profile of the contrast medium in at least one predetermined body region is determined in at least one plane, and the functional parameters of a prediction model that maps or at least approximates the relationship between the profile of a contrast medium injection and the temporal profile of the contrast medium concentration in the predetermined body region are determined from the measured profile of the contrast medium concentration in relation to the profile of the test bolus injection.

Furthermore, the invention also generally relates to a medical system for providing tomographic pictures of a patient. For example, it may relate to one using a contrast medium injection, having at least a recording system with detector, a controllable contrast medium injector, and an arithmetic logic and control unit with stored computer programs that during operation control the recording system and the contrast medium injector and calculate the tomographic images.

BACKGROUND

Because of the low contrasts occurring in specific body regions, it is advantageous for the purpose of displaying such regions using tomographic methods, in particular in the field of computer aided tomography or NMR tomography, to apply contrast media in the display process, and thus to obtain a more contrasted image of these body regions. However, contrast media mostly have the disadvantage that they are biologically incompatible, and their dose is therefore to be held as low as possible. Because of the biological variability of the bodies being examined, however, it is not possible to make a sufficiently accurate and generally valid statement on how the concentration profile of a specific contrast medium administration will develop over time at an observed site in the body. Thus, it is necessary in the case of each body examined to use a test injection of a contrast medium or a test bolus administration as a basis for observing the effect thereof, in particular the time profile, following thereupon, of the concentration values at the site of interest in the body to be examined.

In the case of application in conjunction with a CT examination, over a specific time period after the test bolus injection, and with the use of the lowest possible radiation doses, the concentration is measured in this case indirectly via the changes produced there in the HU values. Since only the imaging effect of the contrast medium is of interest, and there is a linear relationship between the imaging action and concentration of the contrast medium, a statement on the absolute concentration of the contrast medium remains open and trivial. Again, the resolution of the images of such a test examination remains low.

It is known for knowledge of the effect of such a test bolus administration and the assumption of a linear cause/effect relationship to be used as a basis for precalculating the effect of a correct or envisaged contrast medium administration, and thus for determining the dose of contrast medium that is required to attain a sufficient image contrast during a tomographic examination. However, in the case of the known method the calculability is limited to a time period that is equivalent to the preceding measurement of a test bolus administration. It is certainly possible to interpolate values in this time span, but extrapolating beyond the test time period, specifically in both time directions, is possible only in a very limited fashion. Where there has been a need for any type of reasons for the test measurement to be limited in time, the prediction time period largely to be assumed as reliable has so far also been correspondingly limited.

Specific reference is made to the patent applications (not prior publications) with file references DE 10 2005 006 659.3 and 10 2005 006 657.7. The disclosure content of each of these references is incorporated in this application by reference in their entirety, and specifically with regard to the precalculation of a required contrast medium flow on the basis of a known cause/effect relationship of a previously administered test bolus for the purpose of achieving a desired contrast in an observed region of an examined patient, in particular the calculation formulas represented there.

The previously cited applications also only disclose how it is possible to calculate a required contrast medium administration. The interaction of the calculation method with the planning of a tomographic examination is not specified. All that is known so far is a manual calculation and subsequent manual transfer of the calculated parameters to the automatic control of a contrast medium injector. Such a transfer is time consuming and contains many sources of error.

SUMMARY

At least one embodiment of the invention describes a method and/or a system that enable calculated data for contrast medium administration to be transmitted more quickly and while avoiding error for the purpose of carrying out a tomographic examination.

The inventors have realized that it is possible for the method known per se, with the precalculation of required contrast medium administrations during tomographic examinations based on previously specified required contrasts, to be applied substantially more quickly and reliably when, on the one hand, an automatic calculation of a required contrast medium flow takes place and, on the other hand, the parameters resulting in the calculation for the contrast medium flow are also automatically included in carrying out the tomographic examination, the temporal tuning with reference to the start of the tomographic scan and the start of the contrast medium injection, and the profile thereof, being performed automatically.

In accordance with this realization, the inventors propose an improvement in at least one embodiment, of the method known per se, for providing tomographic pictures of a patient with the aid of a tomographic system by using contrast medium injections, wherein the patient is firstly injected with a defined test bolus, while the temporal concentration profile of the contrast medium in at least one predetermined body region is determined in at least one plane, and the functional parameters of a prediction model that maps or at least approximates the relationship between the profile of a contrast medium injection and the temporal profile of the contrast medium concentration in the predetermined body region are determined from the measured profile of the contrast medium concentration in relation to the profile of the test bolus injection. An improvement of the method, in at least one embodiment, resides in the fact that after the specification of a desired contrast in the predetermined body region the profile of a contrast medium injection that is required therefore is automatically calculated in relation to the scan, and the start of the tomographic scan and the start of the contrast medium injection and the profile thereof are started automatically in a fashion temporally tuned to one another.

For the purpose of this application, contrast is understood as the contrast in the pictorial illustration of the tomographic recording, which is directly related to the contrast medium concentration in the body.

In an example design of at least one embodiment of the invention, the functional parameters are stored in a patient-specific fashion, preferably in conjunction with the prediction model used, from the test bolus injection, such that once having been measured the values are also available for later examinations.

In addition to the storage of the functional parameters from the test bolus injection, it is also possible to store the profile of the test bolus injection and the concentration profile of the contrast medium in a patient-specific fashion with designation of the injection site and the measurement site.

In order to improve a later examination, the functional parameters determined by the test bolus injection can be additionally corrected by way of the contrast data determined during the actual contrast medium injection. An additional reliability is thereby created for further examinations, it being possible for the corrected functional parameters likewise to be stored in a patient-specific fashion, preferably in conjunction with the prediction model used.

In a further variant of the method according to at least one embodiment of the invention, the inventors propose that the contrast profile based on a test bolus injection is determined at a number of body regions in the same scanning plane or different scanning planes, and the optimum contrast medium profile for the several body regions is determined. It is possible thereby by giving a single test bolus injection for a number of body regions at the same time that are to be examined to determine the contrast medium profile resulting therefrom such that the entire examination can be carried out with the aid of a single contrast medium administration that is, however, sufficient for all body regions that are to be examined. Furthermore, depending on the body regions being examined it can be necessary to lengthen the time of the contrast medium administration in order to achieve a sufficient image contrast during the scanning time for all body regions being examined. Overall, this method can be substantially more advantageous with reference to the total amount of contrast media used than a graduated examination in which the individual regions are examined sequentially in time with an individually optimum contrast medium administration in each case.

In the case of a CT examination, the several scanning planes can, for example, be examined simultaneously by using a CT system having a twofold or threefold x-ray tube/detector system, the x-ray tube/detector system here scanning a dedicated scanning plane for the test bolus examination.

It is proposed furthermore, that in order to calculate the optimum contrast medium profile minimum values are defined for the contrast that is to be achieved, and a contrast medium profile is determined that fulfills these minimum values in all body regions considered. It is proposed furthermore, that in order to calculate the optimum contrast medium profile minimum values are defined for the duration of the contrast that is to be achieved, and a contrast medium profile is determined that fulfills these temporal minimum values in all the body regions considered.

In addition, it is possible to use a prediction model that includes hemodynamic parameters, preferably the heart time volume, and these are determined with the aid of the test bolus injection and/or the contrast medium injection during the examination scan and are output to the operator. Additional useful information relating to the patient can be obtained in this way without additional further examination.

It may be pointed out that the method according to at least one embodiment of the invention can be applied in conjunction with a CT examination, a PET examination or an NMR examination.

Furthermore, in order to avoid later double examinations and unnecessary stressing of the patient, there is the possibility that the patient-specific data are stored on a chip card dedicated to the patient, particularly with reference to the test bolus injection and/or contrast medium injection. It is thereby possible that even given a change of location of examination the patient can also use the data in other examinations once they have been obtained. For example, it is possible thereby to dispense with a further test bolus injection during a further examination with contrast medium.

For the safety of the patient and with knowledge of the toxic effect of the contrast medium in too high a dose, it is proposed furthermore, that an upper limit is prescribed directly or indirectly for the maximum contrast medium flow and/or the applied contrast medium quantity that must not be exceeded during the automatic calculation and/or administration. It is thereby avoided that life threatening states can occur for the patient owing to possible errors in the calculation system or the use of an unfavorable mathematical model and the very automated transmission of the injection parameters used. The upper limit for the maximum contrast medium flow or the applied contrast medium quantity can be determined, for example, on the basis of patient data that are available or are necessarily to be input, preferably the size and/or the weight of the patient.

A further safety aspect in the examination can be achieved by virtue of the fact that the patient's pulse rate is measured during the scan or at least during the contrast medium administration, and the contrast medium supply is stopped automatically and as a matter of priority when a maximum rate is reached.

It is also possible thereby to avoid a possible incompatibility reaction in good time and reliably, or at least to soften it. This maximum rate can also be determined on the basis of patient data that are available or are necessarily to be input, preferably the age, the size and the weight of the patient.

In accordance with at least one embodiment of the inventive method outlined above, the inventors also propose the further development of a medical system for providing tomographic pictures of a patient by using a contrast medium injection, having at least a recording system with detector, a controllable contrast medium injector, and an arithmetic logic and control unit with stored computer programs that during operation control the recording system and the contrast medium injector and calculate the tomographic images, to the effect that computer programs that simulate the method steps of the inventive method outlined above are stored and are run during operation.

In this medical system, it is possible, for example, that the contrast medium injector constitutes an independent program controlled unit that includes a memory for holding injection parameters, and that the injection parameters are automatically passed on by the arithmetic logic and control unit.

In another variant in at least one embodiment, the medical system can be configured such that the contrast medium injector has a control connection to the arithmetic logic and control unit of the tomographic system and is controlled directly thereby.

It is proposed in addition that the medical system has a card reader unit and/or card writer unit for the purpose of transferring and storing patient-specific data.

BRIEF DESCRIPTION OF THE DRAWINGS

The invention is described in more detail below with reference to the example embodiments with the aid of the figures, only the features required for understanding the invention being illustrated, and the following reference symbols being used: 1: CT system; 2: x-ray tube; 3: detector; 4: system axis/z axis; 5: gantry housing; 6: movable patient couch; 7: patient; 8: control line of the contrast medium injection apparatus; 9: control and arithmetic logic unit; 10: control and data line of the gantry; 11: contrast medium injection apparatus; 12: contrast medium supply; 13: flow profile of the test bolus; 14: contrast reaction to the test bolus; 15: required contrast region, prediction; 16: contrast profile; 17: contrast medium flow profile; 101 to 110: method steps; F: flow rate of the contrast medium; HU: Hounsfield units; $Prg_1$-$Prg_n$: computer programs; to: start of the contrast medium injection; $t_1$: end of the contrast medium injection; $t_s$: start of the scan; $t_E$: end of the scan; t: time.

In detail, in the drawings:

FIG. 4 shows an example flowchart of the inventive method.

DETAILED DESCRIPTION OF THE EXAMPLE EMBODIMENTS

Figure 1:
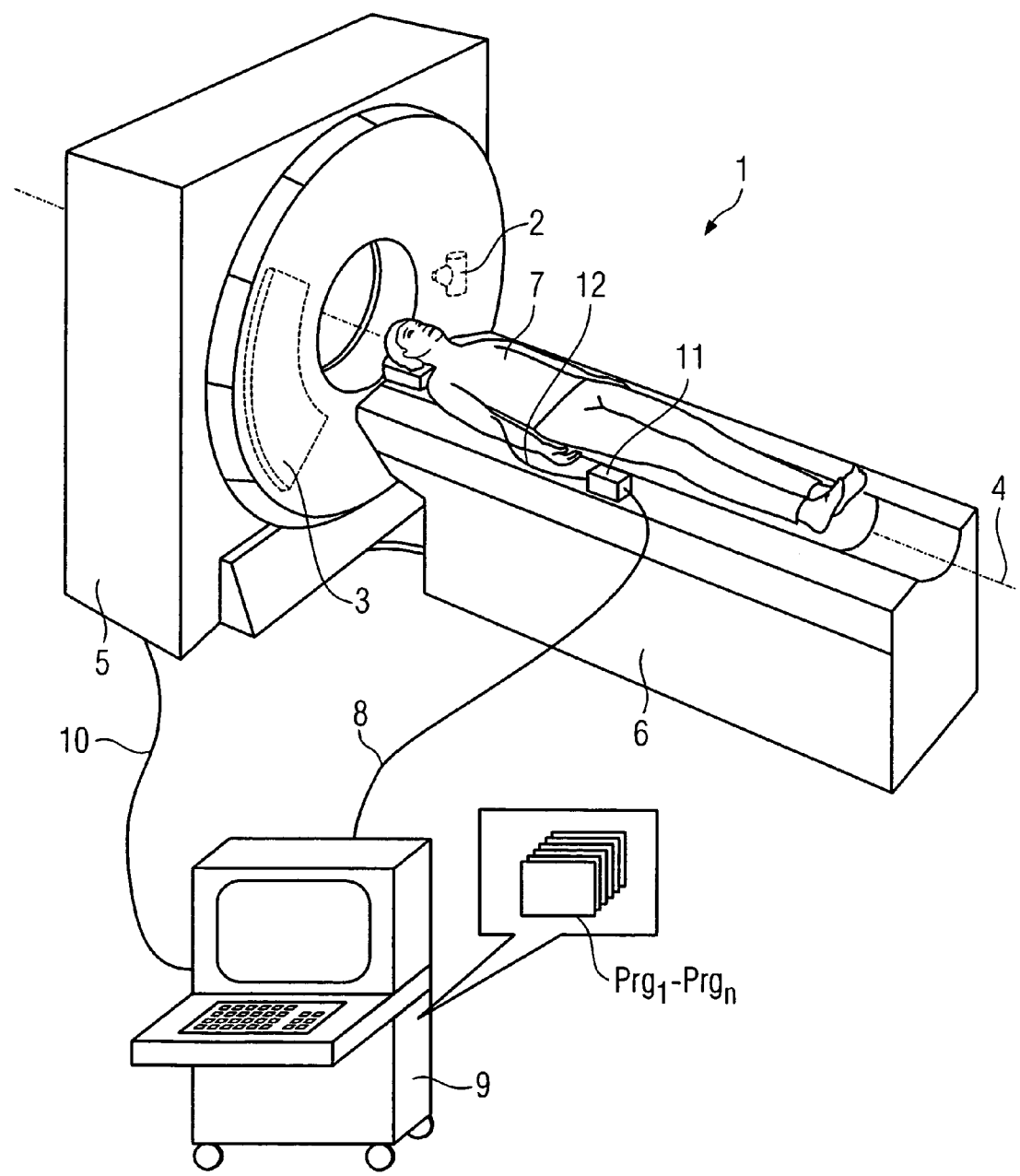
FIG. 1 shows an inventive CT system.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows an inventive CT system 1 having a gantry housing 5 in which an x-ray tube 2 with a detector 3 situated opposite is located in a fashion fastened on a rotating gantry. The x-ray tube 2 and the detector 3 rotate about a system axis 4, while a patient 7 is displaced continuously along the system axis 4 with the aid of a displaceable patient couch 6, and a spiral scan of the patient 7 is thereby carried out. A contrast medium supply 12 is placed on the patient 7 and is supplied with a predetermined contrast medium flow via a controllable contrast medium injection apparatus 11. Starting from this supply of the patient 7, the contrast medium is distributed in the patient's blood circulation and is also distributed to the region essential to the examination, where an appropriate contrast enhancement is caused in the CT image, and the assessment of the CT image is substantially improved thereby. The control of the contrast medium injection apparatus 11 is performed via a control line 8, and the control of the CT system is performed by the control and data line 10 by means of a control and arithmetic logic unit 9. This control and arithmetic logic unit 9 includes, inter alia, sufficient storage space for holding computer programs $Prg_1$ to $Prg_n$ that are used to control the CT system and the subsequent data evaluation.

Figure 2:
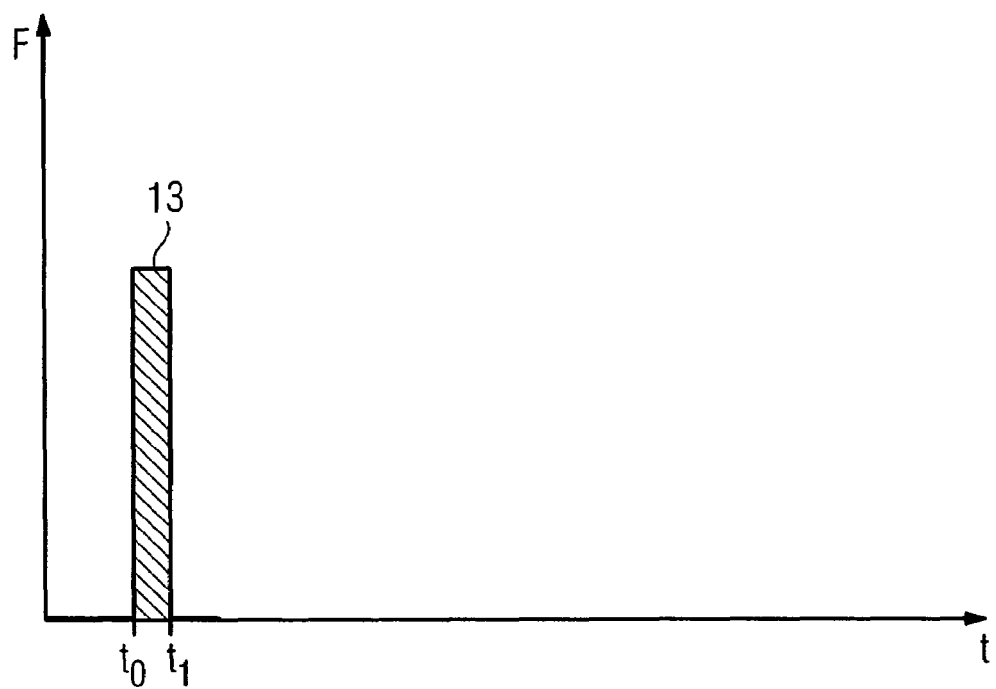
FIG. 2 shows a comparison of test bolus injection and contrast response in the CT image.
Figure 2:
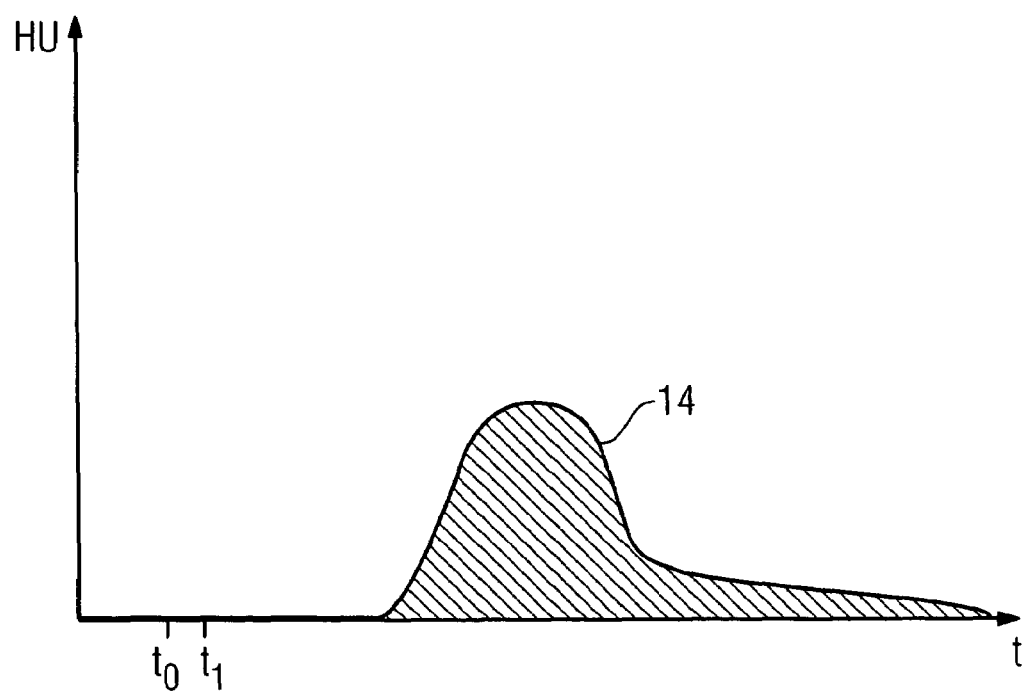

A test bolus injection and the contrast reaction following thereupon in a CT image are illustrated by way of example in FIG. 2 in two coordinate systems arranged one above another. In both coordinate systems, the time axis t is plotted on the abscissa, while the upper coordinate system represents the flow rate $F_T$ on the ordinate, and in the lower coordinate system the Hounsfield units HU are plotted on the ordinate. Injected at the instant $t_0$ is a test bolus 13 that applies a small quantity of contrast medium to the blood circulation of the patient at a defined flow rate over a specific time. In the coordinate system lying therebelow, a rise in the contrast is to be seen after a certain delay, the contrast medium profile 14 being illustrated as the effect relating to the injected test bolus 13. Because of the functional relationship between the test bolus injection and the subsequently determined contrast reaction in the tomographic image, here a CT image, it is possible, as described in detail in the two patent applications cited at the beginning, to make a prediction as to a how a contrast medium injection must be provided in order to achieve a desired contrast profile in the CT image.

Figure 3:
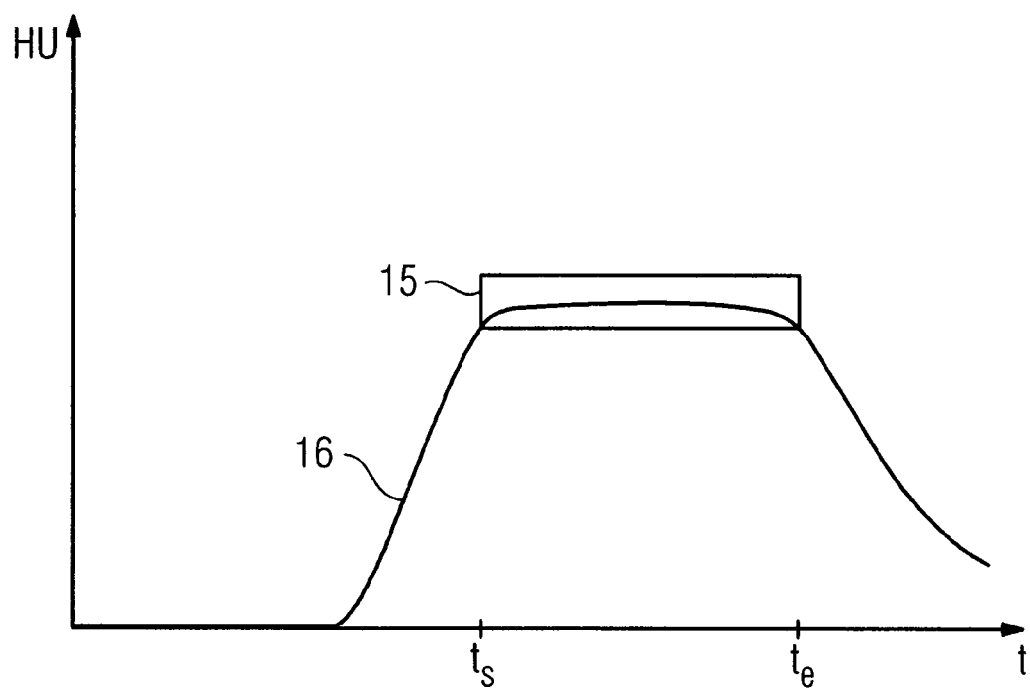
FIG. 3 shows a calculated contrast medium flow for the examination, together with a contrasting contrast profile in the CT image.
Figure 3:
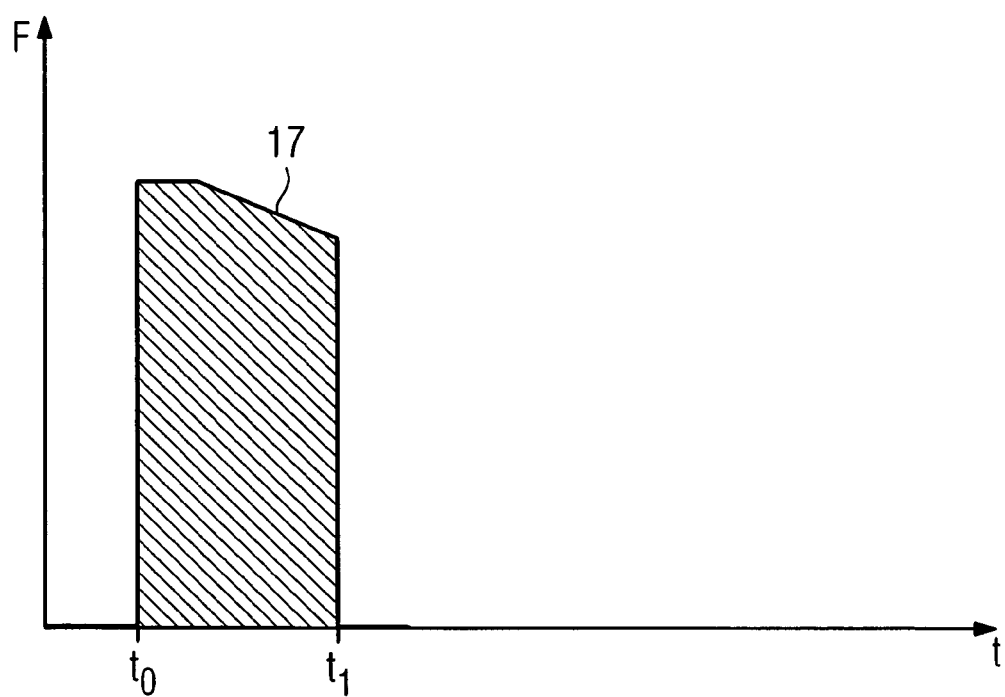

FIG. 3 shows the inventive procedure in accordance with which—as illustrated in the upper coordinate system—the desired contrast region 15 in a CT image is firstly prescribed by the user, the prescription specifying both the intensity of the contrast in HU units and the time duration with the start instant $t_s$ and the end instant $t_e$.

On the basis of the functional relationship now known between a contrast medium injection and the contrast reaction, following thereupon, in the CT image, it is now possible to calculate how the contrast medium flow 17—illustrated in the lower coordinate system—must appear in order to achieve at the desired region of the patient in a CT image or some other tomographic image a contrast profile 16 that lies in the specified region 15. The latter is calculated in accordance with the functional relationships, and according to the invention the contrast medium injection apparatus is controlled in such a way that such a contrast medium flow 17 is set up both with reference to its flow profile and with reference to the temporal coordination between the start of the contrast medium injection $t_0$ and the desired scan start $t_s$. Of course, this also includes the desired temporal coordination between the scan end $t_e$ and the end of the contrast medium flow $t_1$ in this precalculation.

An example sequence of the inventive method is illustrated in the flow chart of FIG. 4, an example variant being selected here in which the response of the test bolus injection at two different points of the body is examined, and an optimum contrast medium injection is subsequently selected automatically.

In method step 101, the operator gives the start command to begin the procedure of the test bolus injection, in which case, of course, he must previously have informed the system of those body regions at which the result of the test bolus injection is to be observed. If these different body regions lie in the region of a single scan slice, the possibility exists of tracking the results of the test bolus injection with the aid of a single tube/detector system and a detector that is narrow in the Z direction. However, the possibility also exists of using a CT system that has a number of tube/detector systems that can be set up on different slice planes, or there is also an alternative possibility of using a tube/detector system having a detector that is very wide in the Z direction and in the case of which, for example, two slice planes further removed from one another are observed through variable slit stops such that even body regions in different slices can be considered.

After this preliminary work has been concluded, and the operator has instituted the beginning of the test procedure in step 101, the test bolus injection by the CT system is automatically started in step 102, the two regions under consideration being observed in parallel with one another in step 103 and in step 105, and the reaction of the test bolus injection in these body regions being recorded with reference to the variation in a contrast and the time profile thereof. The evaluation is subsequently performed in the parallel steps 104 ands 106, an optimum profile of a contrast medium injection being precalculated for each observed body region. These two required contrast medium injections are compared in step 107 in order to achieve the desired result, it now being possible to tune the separately calculated contrast medium injections to one another such that the entire examination can be carried out with a single contrast medium injection that respectively contains the minimum quantities of the two precalculated variants.

Subsequently, the contrast medium injection is started automatically with an automatic time-offset start of the CT scan, the evaluation of the image results in the desired examination region taking place in steps 108 and 109, and it also being possible to determine additional hemodynamic values in step 110. These can originate, for example, from the test bolus injections that are corrected once again if appropriate on the basis of the contrast medium injection that follows later. For example, this can involve the heart time volume that can be determined from the functional relationship between the contrast medium injection and the contrast medium reaction in the CT picture.

Thus, it is possible with the aid of this method to find out the optimum, more precisely the optimally low, contrast medium consumption and, at the same time, to achieve a good image quality in a reliable way, the stressing of the patient being minimal here. This calculation can be performed in a patient-specific fashion and, if appropriate, it is even possible to dispense with a test bolus injection on the basis of previous examinations. Moreover, the workload on the operator is substantially less, since the calculation and planning are performed automatically as a result of which the examination can be performed substantially more quickly overall, and care is taken to ensure that maloperation in conjunction with the contrast medium injection is largely avoided.

It goes without saying that the abovenamed features of the invention can be used not only in the respectively specified combination, but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for a tomographic scan, the method comprising:

determining, while a patient is injected with a defined test bolus, a temporal concentration profile of a contrast medium in a number of body regions in different scanning planes using a test tomographic scan;

determining functional parameters, of a prediction model that at least approximates the relationship between a profile of a contrast medium injection and the temporal concentration profile of the contrast medium in the body regions, from the determined temporal concentration profile of the contrast medium in relation to a profile of the test bolus injection;

determining a desired contrast for the body regions;

calculating the profile of the contrast medium injection in temporal relationship with the test tomographic scan automatically based on the determined desired contrast, wherein the calculation of the contrast medium injection profile includes defining temporal minimum values for a duration of the desired contrast, the contrast medium injection profile satisfying the temporal minimum values in all of the body regions; and producing a picture for each of the body regions based on an examination tomographic scan using the calculated contrast medium injection profile, wherein a start of the examination tomographic scan and a start of the contrast medium injection and the profile thereof occurs automatically in a manner temporally tuned to one another based on the automatically calculated profile of the contrast medium injection, and the contrast medium injected in the examination tomographic scan is first injected into the body regions, after calculating the profile of the contrast medium injection.

2. The method as claimed in claim 1, wherein the functional parameters are stored in a patient-specific fashion.

3. The method as claimed in claim 1, wherein the profile of the test bolus injection and the temporal concentration profile of the contrast medium are stored in a patient-specific fashion with designation of an injection site and a measurement site.

4. The method as claimed in claim 1, wherein the functional parameters determined by the test bolus injection are corrected by use of contrast data determined during an actual contrast medium injection.

5. The method as claimed in claim 4, wherein the corrected functional parameters are stored in a patient-specific fashion.

6. The method as claimed in claim 1, wherein, in the case of a CT examination, the scanning planes are scanned by use, in each case, of an x-ray tube detector system angularly offset from another x-ray tube detector system.

7. The method as claimed in claim 1, wherein the prediction model includes hemodynaniic parameters and the parameters are determined with the aid of at least one of the test bolus injection and the contrast medium injection during the examination scan and are output to the operator.

8. The method as claimed in claim 1, wherein the tomographic scan includes using at least an x-ray tube and an x-ray detector.

9. The method as claimed in claim 1, wherein the tomographic scan includes using at least one PET detector.

10. The method as claimed in claim 1, wherein the tomographic scan includes using an NMR system.

11. The method as claimed in claim 1, wherein patient-specific data is stored on a chip card dedicated to the patient.

12. The method as claimed in claim 1, wherein an upper limit is prescribed directly or indirectly for at least one of a maximum contrast medium flow and an applied contrast medium quantity that is not exceeded during at least one of the automatic calculation and injection.

13. The method as claimed in claim 12, wherein the upper limit is determined on based on patient data that is available.

14. The method as claimed in claim 1, wherein a pulse rate of the patient is measured during at least one of the scan and the contrast medium injection, and a contrast medium supply is stopped automatically when a maximum pulse rate is reached.

15. The method as claimed in claim 14, wherein the maximum pulse rate is determined based on patient data that is available.

16. A medical system, comprising:
a recording system with a detector;
a controllable contrast medium injector; and
an arithmetic logic and control unit including stored computer programs stored on a computer-readable medium that, during operation, control the recording system and the contrast medium injector and calculate tomographic images, the computer programs being configured, when run during operation, to execute the method of claim 1.

17. The medical system as claimed in claim 16, wherein the contrast medium injector is an independent program controlled unit that includes a memory for holding injection parameters that are transmitted by the arithmetic logic and control unit.

18. The medical system as claimed in claim 16, wherein the contrast medium injector includes a control connection to the arithmetic logic and control unit, the contrast medium injector being controlled by the arithmetic logic and control unit.

19. The medical system as claimed in claim 16, wherein at least one of a card reader unit and card writer unit is connected to transfer and store patient-specific data.

20. The method as claimed in claim 1, wherein the functional parameters are stored in a patient-specific fashion, in conjunction with the prediction model used, from the test bolus injection.

21. The method as claimed in claim 2, wherein the profile of the test bolus injection and the concentration profile of the contrast medium are stored in a patient-specific fashion with designation of an injection site and a measurement site.

22. The method as claimed in claim 4, wherein the corrected functional parameters are stored in a patient-specific fashion, in conjunction with the prediction model used.

23. The method as claimed in claim 12, wherein the upper limit is determined on the basis of at least one of the size and weight of the patient.

24. The method as claimed in claim 14, wherein the maximum rate is determined on the basis of at least one of the age, size and weight of the patient.

25. The medical system as claimed in claim 17, wherein at least one of a card reader unit and card writer unit is connected to transfer and store patient-specific data.

26. The medical system as claimed in claim 18, wherein at least one of a card reader unit and card writer unit is connected to transfer and store patient-specific data.

* * * * *